US008682691B2

(12) United States Patent
George et al.

(10) Patent No.: US 8,682,691 B2
(45) Date of Patent: Mar. 25, 2014

(54) HEALTH QUALITY MEASURES SYSTEMS AND METHODS

(75) Inventors: Jibu George, Bensalem, PA (US); Bryan Rosenberger, Pennsburg, PA (US); Charlie Jarvis, Toms River, NJ (US)

(73) Assignee: QSI Management, LLC, Irvine, CA (US)

( * ) Notice: Subject to any disclaimer, the term of this patent is extended or adjusted under 35 U.S.C. 154(b) by 176 days.

(21) Appl. No.: 13/234,999

(22) Filed: Sep. 16, 2011

(65) Prior Publication Data

US 2012/0065998 A1 Mar. 15, 2012

Related U.S. Application Data

(63) Continuation-in-part of application No. 12/721,043, filed on Mar. 10, 2010.

(60) Provisional application No. 61/159,327, filed on Mar. 11, 2009.

(51) Int. Cl.
*G06Q 50/00* (2012.01)
(52) U.S. Cl.
USPC .............................................................. 705/2
(58) Field of Classification Search
USPC .................. 705/2, 3; 709/246; 395/800.18
See application file for complete search history.

(56) References Cited

U.S. PATENT DOCUMENTS

| 5,765,014 A | * | 6/1998 | Seki ................................ 712/18 |
| 2006/0173716 A1 | | 8/2006 | Wang |
| 2006/0282286 A1 | | 12/2006 | Faris, III et al. |
| 2007/0061393 A1 | | 3/2007 | Moore |
| 2007/0078680 A1 | | 4/2007 | Wennberg |
| 2007/0180150 A1 | * | 8/2007 | Eisner et al. .................. 709/246 |
| 2008/0208813 A1 | | 8/2008 | Friedlander et al. |
| 2008/0215370 A1 | * | 9/2008 | Dent et al. ........................ 705/3 |
| 2009/0076841 A1 | * | 3/2009 | Baker et al. ....................... 705/2 |

OTHER PUBLICATIONS

Wikipedia "reverse polish notation".*

* cited by examiner

*Primary Examiner* — John Pauls
(74) *Attorney, Agent, or Firm* — Fish & Associates, PC

(57) ABSTRACT

Systems and methods of exchanging Healthcare Quality Measures (HQM) are disclosed. Healthcare providers can define one or more HQMs by constructing expressions using an expression builder according to a funding organization's requirements. The expression builder advantageously allows the Healthcare provider to build measure expressions without the need to know a complex programming language. Once a measure is derived, it can be converted to a common HQM data format and exchanged with the organization via an intermediary HQM service. The HQM data can then be converted into the organization's proprietary format. Thus, HQM data exchanges among providers and organizations are simplified.

14 Claims, 6 Drawing Sheets

Method 500

Interface 600

Interface 700

Parse and Evaluate the Expression into
Lists in Memory
        [Age on Visit] >= 18 & [Age on Visit] <= 75
        >> becomes >>
Select personid from HQM where [Today-DoB] >= 18 OR [Today-DoB] <= 75

Figure 7

Interface 800

Internally List Output Expressed for HQM Denominator
(( { (List1 & List2) or (List3 or List4) } & { (List5 & List6 )} ) & List7)

Infix Notation changed to Computer Processible Postfix Notation Reverse Polish Algorithm HQMList_1 HQMList_2 X HQMList_3 HQMList_4 X U HQMList_5 HQMList_6 X X

Figure 8

Interface 900

Figure 9

HEALTH QUALITY MEASURES SYSTEMS AND METHODS

This application is a continuation-in-part of U.S. patent application Ser. No. 12/721,043, filed on Mar. 10, 2010 which is a non-provisional of U.S. Provisional Application No. 61/159,327, filed on Mar. 11, 2009.

FIELD OF THE INVENTION

The field of the invention is healthcare data flow and management.

BACKGROUND

Health organizations require healthcare providers to submit measures of the provider's performance for various reasons. One reason includes tracking provider performance measures over time to ensure quality care is provided. Another reason includes ensuring that providers meet any requirements to receive funds (e.g., grants, reimbursement, incentives, etc). Regardless of the reasons, the known reporting systems are difficult to use and are highly inefficient.

Others have put forth effort toward coordinating communications among healthcare entities. For example, the following reference describe various aspects of healthcare quality management:

U.S. patent application publication to Wang titled "Systems and Method for Real Time Regional Feedback", filed Jan. 30, 2006, describes a system that provides for monitoring of healthcare quality measures across organization boundaries. The contemplated system allows organizations to align themselves with the industry's leading performers.

This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

U.S. patent application publication to Faris et al. titled "Evidence-Based Quality Improvement and Risk Management Solutions Method", filed Jun. 14, 2005, describes a tool selection system that selects tools to improve quality based on evidence from literature. The selection process can include determining national authoritative healthcare quality measures.

U.S. patent application publication to Moore titled "Management of Health Care Data", filed Feb. 1, 2006, provides for systems and methods of syndicating healthcare data among collaborators.

U.S. patent application publication to Wennberg titled "Systems and Methods for Analysis of Healthcare Provider Performance", filed Oct. 3, 2006, discusses using healthcare measures, both expected and actual, to determine if some services are unwarranted.

U.S. patent application publication to Friedlander et al. titled "System and Method for Quality Control in Healthcare Settings to Continuously Monitor Outcomes and Undesirable Outcomes such as Infections, Re-Operations, Excess Mortality, and Readmissions", filed Apr. 27, 2007, describes a probability analysis system that can be used within a healthcare quality measure environment.

U.S. patent application publication to Baker et al. titled "Rules-Based Software and Methods for Health Care Measurement Applications and Uses Thereof", filed Dec. 7, 2007, describes a system that converts healthcare data into healthcare measures.

One problem with existing systems is that they fail to account for the expansive number of reporting channels among providers and/or organizations. A provider could engage with five, ten, twenty, or more organizations, while an organization could literally interface with hundreds of providers. The sheer number of engagements and communication channels is overwhelming in such a many-to-many environment. It's no wonder such communication exchanges are prone to data errors.

The issues surrounding many-to-many communication exchanges in the medical field are exacerbated by the myriad of data formats that are required for reporting healthcare quality measures (e.g., metrics). A provider is required to report measures according to five, ten or more different data formats as required by various organizations. This places an undue burden on the providers, especially smaller providers, private practices for example. Of course the reverse is true as well. An organization engages with many different providers where each provider prefers to utilize their own reporting formats.

Another problem is that each organization has proprietary requirements for establishing a measure (e.g., a metric) of performance. A provider could easily be required to submit hundreds, if not thousands of different measures across multiple organizations, where each measure has a complex set of requirements. Providers must spend considerable amounts of time to ensure they are reporting a proper measure to the correct organization.

Yet another problem associated with existing Healthcare Quality Measure (HQM) reporting solutions is that the solutions require a provider to have access to highly skilled computer labor to compile, analyze, and produce measure reports. Known systems require a provider to install and manage highly complex databases, query the databases using arcane SQL statements, and compile reports according to the various formats discussed above. The skills required for such work are often beyond the capability of a provider or beyond a provider's budget for hiring skilled labor. Unfortunately, most providers simply cannot provide reports, thereby reducing their chances of obtaining funding, grants, incentives, or other benefits.

The above issues combine to create additional problems, even for those providers that do have access to the necessary skilled labor. The voluminous number of measures coupled with reporting requirements results in the provider lacking sufficient time (1) to compile relevant encounter data from their databases of patient and encounter data, (2) to analyze the compiled data to derive measures, and (3) to provide the results to the various organizations according to preferred formats. Most providers simply lack time or resources to report to all desirable organizations in a timely fashion.

Thus there is a still considerable need systems, configurations, or methods for providing healthcare quality measure (HQM) reports that addresses the above issues.

SUMMARY OF THE INVENTION AND EMBODIMENTS

The present inventive subject matter is drawn to systems, configurations, and methods of providing HQM reports from healthcare providers to healthcare organizations. In a preferred embodiment, the issues surrounding the many-to-many communication exchanges can be alleviated through the use of an intermediary HQM service. The HQM service preferably offers capabilities to convert or translate a provider's patient and encounter data from a proprietary format to a common HQM format. Furthermore, HQM service also allows a provider to define one or more measures easily that conforms to the requirements of remote healthcare organizations. Preferred HQM services also provide reporting modules configured to submit reports having proper measures to the various organizations. The contemplated HQM service streamlines the measure reporting process to ensure that providers submit correct measures in the correct format to the proper organizations in a timely fashion.

Healthcare providers represent entities that aid individuals with their health related needs. Providers can be an individual person, a business, an organization, or other entity. Example providers include doctors, nurses, private practices, clinics, hospitals, aid organizations (e.g., Doctors without Boarders), etc.

Healthcare organizations represent entities that monitor or fund providers. The term "organization" is used euphemistically, and should be considered to include any group (e.g., a business, organization, foundation, person, etc.). Example healthcare organizations include city, state, or federal governments, foundations, granting organizations, universities, or other organizations that likely act in a funding or sponsor capacity.

As used herein, a "measure" represents a metric of performance for a provider. In some embodiments, a measure is a ratio of a number (numerator) of patient encounters satisfying selection criteria associated with a type of care, to the number (denominator) of a base set of patient encounters. A preferred measure also comprises one or more lists of entries representing encounters, where the lists can correspond to the various selection criteria. Providing the contemplated lists, preferably through the HQM service and its associated HQM analysis modules, allow organizations to drill down into the measure data as opposed to merely receiving a number.

BRIEF DESCRIPTION OF THE DRAWING

FIG. 7 is an interface for converting and displaying a measure expression as SQL queries.

FIG. 8 is an interface for converting and displaying a measure expression in postfix notation.

FIG. 9 is an interface for displaying patient counts and lists.

DETAILED DESCRIPTION

It should be noted that while the following description is drawn to a computer/server based work package processing system, various alternative configurations are also deemed suitable and may employ various computing devices including servers, interfaces, systems, databases, agents, peers, engines, controllers, portals, platforms, modules, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network. One should also appreciate that the disclosed techniques increase an efficiency of communicating healthcare data among a distributed set of healthcare entities (e.g., providers, organizations, services, etc.).

Figure 1:
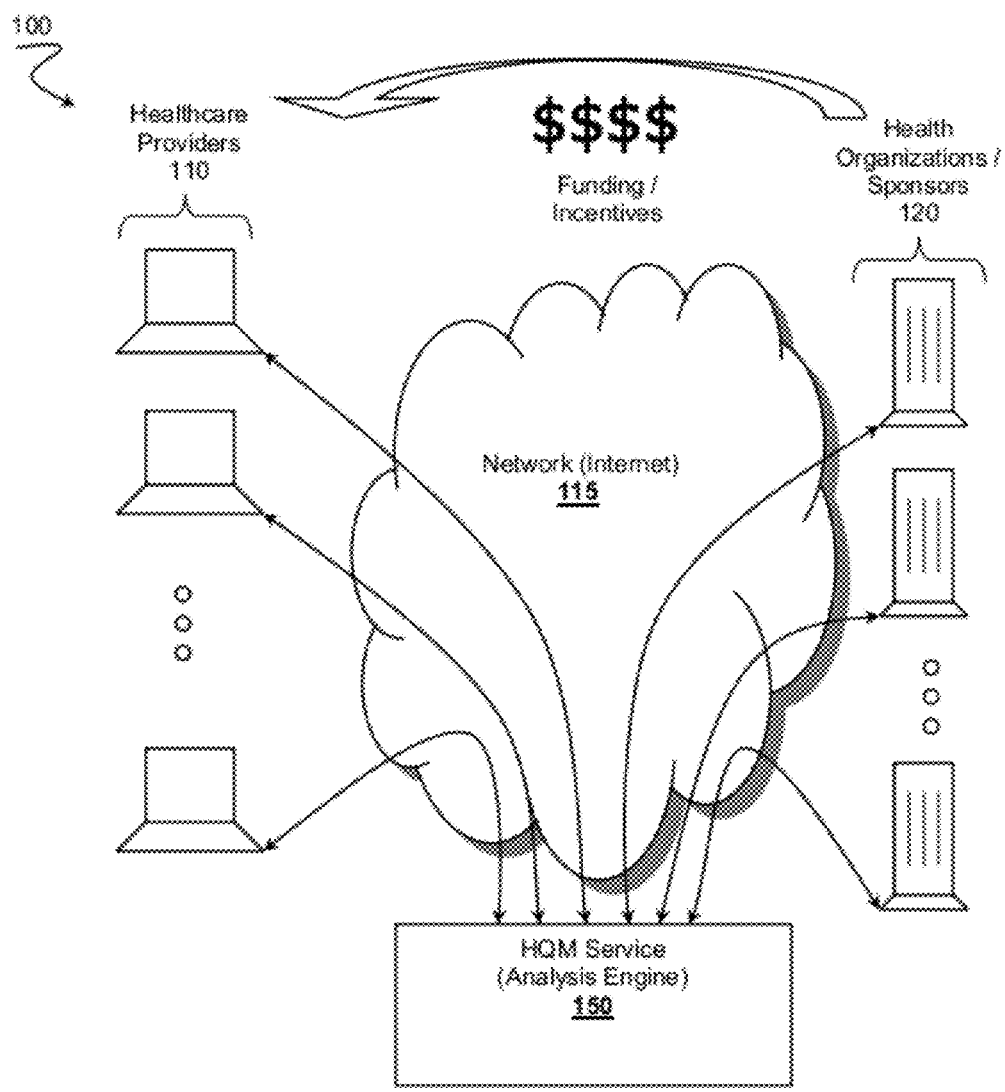
FIG. 1 is a schematic overview of a contemplated HQM system.

FIG. 1 provides a schematic overview of a contemplated HQM system 100. Multiple, unrelated healthcare providers 110 exchange HQM data 130 with multiple, unrelated health organizations 120 via an intermediary HQM service 150. The HQM service 150 provides for normalizing the various data formats, measure requirements, or reporting requirements among the participants in the HQM community. Communications, reporting, or other data exchanges preferably occur over a packet switched network 115 (e.g., the Internet, LAN, WAN, WLAN, etc.). The HQM service 150 essentially eliminates most of the many-to-many communication exchange issues by flattening the communication space among the various participants. By reducing the hurdles for reporting measures to funding sponsors 120 or other organizations 120, providers 110 are able to quickly and efficiently receive funding or incentives from the organizations.

Patient or encounter data can be stored in one or more databases. Any suitable database can be used as desired. Example databases include Access, MySQL, PostgreSQL, or other commercially available database. As used herein "database" should be construed to mean a computing device configured to store and retrieve data from a storage device (e.g., HDD, SSD, CD, DVD, NAS, SAN, RAID system, etc.).

Although FIG. 1 illustrates an embodiment where an HQM service 150 is accessed by the participants of the HQM community over the Internet, it is specifically contemplated that the various combinations features, capabilities, interfaces, modules, or other elements of the service can be implemented local to each site. For example, many of the analysis aspects of the service 150 could be installed local to a provider site 110.

Figure 2:
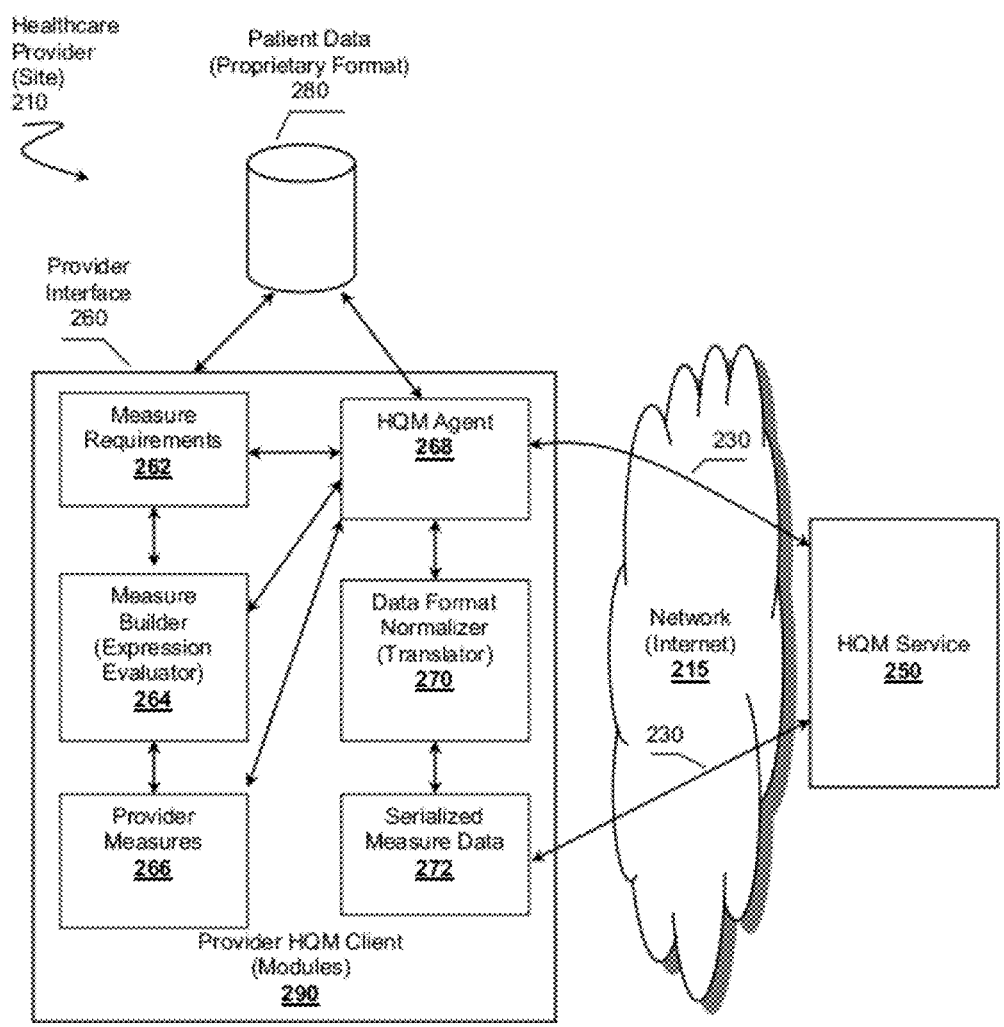
FIG. 2 is a schematic of a healthcare provider client interface to an HQM service.

FIG. 2 presents an overview of a healthcare provider site 210 where a provider utilizes a provider HQM interface 260 to access one or more capabilities of the HQM system, assuming proper authentication. As used herein the term "interface" should be considered a computing device or computing component configured to execute software instruction stored on computer readable media. The HQM interface 260 is configured to allow a provider to enter or to receive HQM related data 230 from the HQM system. Example provider HQM interfaces 260 include computers with web browsers, web services application program interfaces (API), network interfaces, or other similar interfaces that are configured to present HQM information.

Preferably provider interface 260 includes the capability of receiving an organization's measure requirements 262, possibly from the HQM service 250. The service 250 can exchange measure requirements 262 among the various participants via a common HQM format to reduce risk of provider confusion. This ensures that the provider 210 can easily leverage their experience working on measures from a first organization to those of a second organization, without having to learn new measure formats or requirements. The provider 210 can use the interface 260 to access a measure builder 264 that allows provider 210 to define a measure 266 that pertains to the provider's patient data 280, regardless of the proprietary format of the data 280. Once defined, the measure 266 can be derived.

One acceptable measure builder 264 can include Next-Gen™ Expression Evaluator. A preferred measure builder 264 reduces a requirement that a provider needs highly skilled technical labor by offering the provider 210 several enhanced capabilities. For example, the measure builder 264 can utilize a data format normalizer 270 (e.g., a translator) that can automatically convert encounter data 280 from a provider's data format to the common HQM format. Another capability allows the provider to drag-and-drop, or to point-and-click in order to modify elements of a measure expression to build a measure 266, without requiring the provider 210 to draft complex SQL queries. The expression elements can include parameters, constants, lists of encounter entries to be processed or analyzed, operators, or other expression elements.

In some embodiments, the HQM service 250 communicates with a HQM agent 268 that is configured to exchange data 230 with the remote HQM service 250 and with the provider 210 via the provider interface 260. The agent 268 can receive provider-defined measures 266 and possibly derive the actual measures from the patient data 280. Once the measure information is collected from the patient data 280, the agent can normalize the data into a common HQM data format (e.g., serialized measure data 272) via the data format normalizer 270. The measure information can be serialized, possibly using XML or other serializing format, and sent back as data 230 over a network 215 to the HQM service 250.

One should appreciate that the provider HQM interface 260 can be embodied by a computer system having one or more HQM client software modules 290 installed. Alternatively, the computer system could include a web browser that accesses the provider interface capabilities from an HTTP server, either locally resident at the provider site 210 or remote from the provider site 210.

Figure 3:
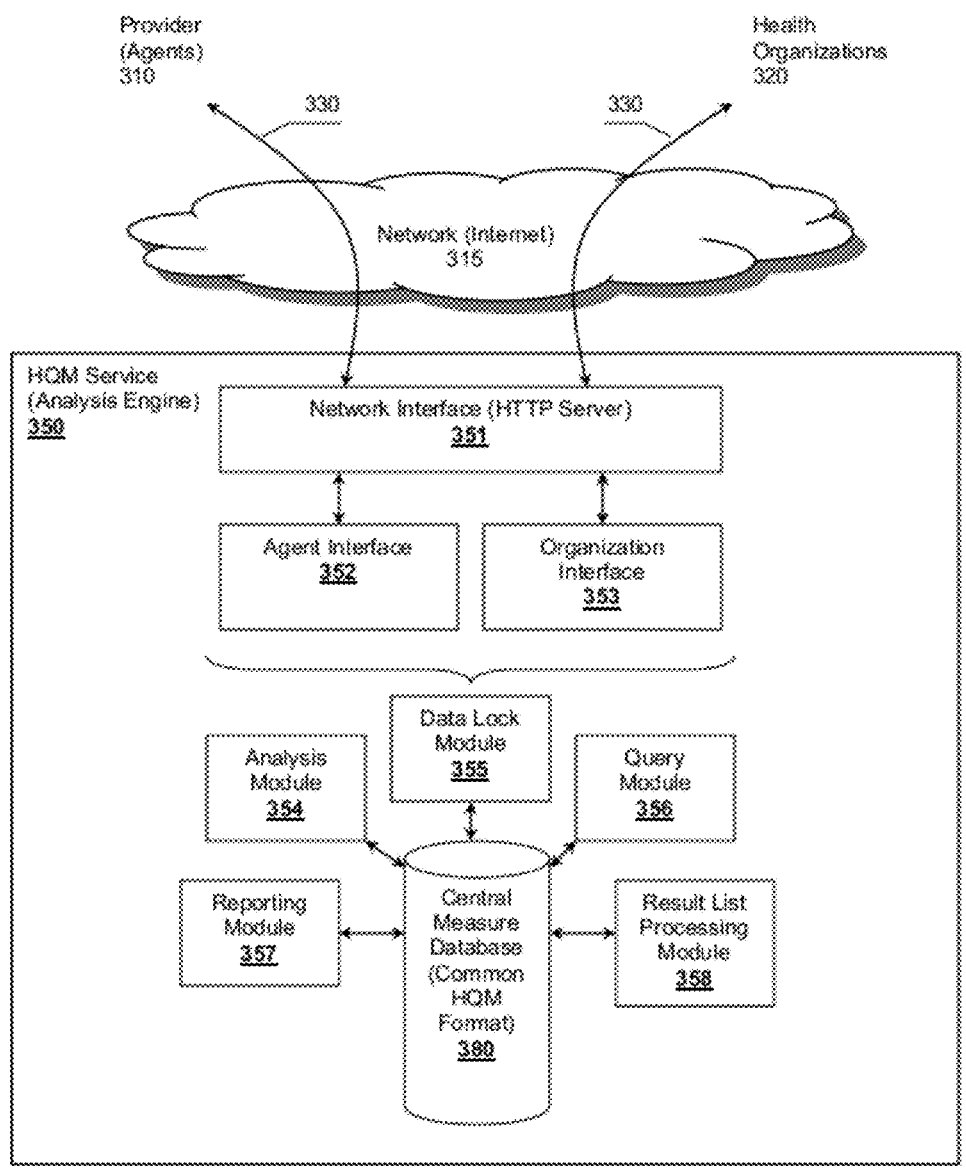
FIG. 3 is a schematic of an HQM service capable of operating as an analysis engine.

FIG. 3 illustrates a possible embodiment of an HQM service 350 implemented as a web service accessible over a network 315. In a preferred embodiment, an HQM service 350 comprises an HQM analysis engine 350 capable of processing various measures from providers 310 as required by various organizations 320. The HQM analysis engine 350 can include a network interface 351, possibly an HTTP server, configured to communicate to remote participants in the HQM community including providers 310 or organizations 320. For example, the analysis engine 350 can utilize an agent interface 352 through which it can exchange data 330 with provider HQM agents (e.g., commands, serialized HQM data, queries, etc.), or other aspect of a provider HQM client. Additionally, the engine 350 can employ an organization interface 353 through which the engine 350 can exchange measure requirements, reports, or other HQM related information with remote organization HQM clients 320.

As used herein, the term "engine" should be considered a computing device configured to execute software instructions stored on a computer readable medium. Preferably the software instructions include HQM analysis capabilities for deriving measures from normalized encounter data obtained from provider's patient databases.

A preferred HQM analysis engine 350 comprises one or more modules capable of interacting with the agent interface or organization interface. Example modules include an analysis module 354 configured to access encounter data stored in a central or remote database 380, and configured to derive one or more measures. Another module can include a reporting module 357 capable of generating a measure report from a derived measure where the report conforms to the reporting requirements of an organization 320. Yet another module can include a data lock module 355 that allows the HQM service 350 to restrict access to data (e.g., encounter or non-encounter data) at a remote site to ensure the data is stable before being downloaded, or uploaded. Still another possible module includes a list processing module 358 used to process result sets as part of a measure, or generated while deriving a measure. Still yet another module can include query module 356 that allows remote participants to submit HQM queries to the engine 350, which can then generate lists (e.g., a result set) that satisfy the query.

In a preferred embodiment, an HQM analysis module 354 derives a measure by applying one or more measure selection criterion to encounter data, possibly stored locally or via an HQM agent at a provider site 310. Preferably, the selection criteria are used to generate one or more lists, each list having entries corresponding to encounters that satisfied the selection criteria. The lists can then be used to derive a measure.

As discussed previously, a provider 310, or other member of the community, can define a measure by creating an expression that can be evaluated. The expression comprises one or more elements of parameters, operators, or other selection criteria that can be used to select data entries from the various databases. The results of applying the expression is preferably a list of database entries from one or more databases representing encounters that satisfy the expression. The lists can then be used for further analysis to derive the measure. The measure can be a simple, single value metric (e.g., ratio of a numerator to denominator), or a multi-valued data set comprising a metric and all the lists, or list entries, that went into forming the measure. In a preferred embodiment, the measure data is stored in the common HQM format.

Once the various lists are generated, they can be processed via the list processing module 358. The list processing module can create new lists, merge lists, prune lists, filter lists, or otherwise support analysis of the data via list processing. It should be appreciated that lists are result sets of filters placed on encounter data, where each entry in the encounter data can be considered an n-tuple. Such an approach provides for quick, efficient analysis of provider performance measures, either automated via the HQM service 350, or even manually by the provider 310 or organization 320.

Figure 4:
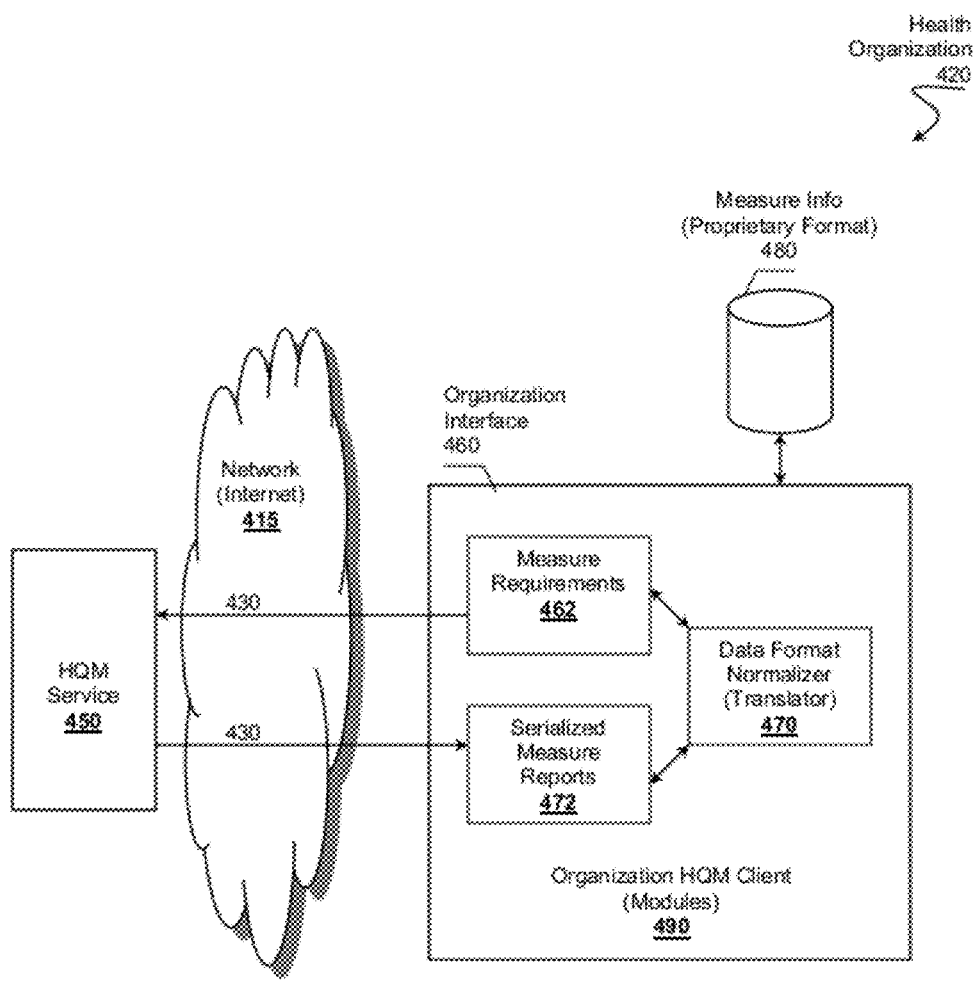
FIG. 4 is a schematic of a healthcare organization client interface to an HQM service.

FIG. 4 illustrates a schematic of an embodiment where a health organization site 420 interfaces with the HQM service 450, assuming proper authentication, via an organization interface 460 represented by an organization HQM client 490. Healthcare data 430 can be exchanged over network 415. In a preferred embodiment the organization interface 460 is configured to send measure requirements 462 or other HQM reporting information to the HQM service 450. Additionally, the organization interface 460 is preferably configured to receive HQM reports 472, possibly in a serialized format. It is also contemplated that the organization interface 460 can include a data format normalizer 470 (e.g., a translator) that can convert from a common HQM data format to a proprietary format used by the organization to store measure information 480. It is even further contemplated that normalizer 470 could convert from one proprietary format to another proprietary format.

Figure 5:
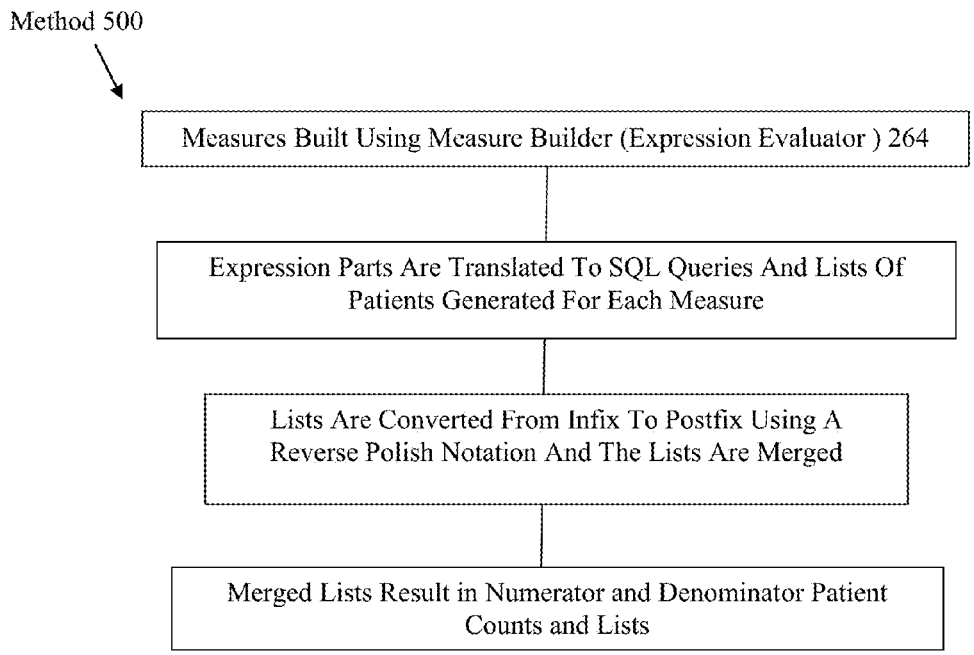
FIG. 5 is a schematic of a method of transforming health quality measurement data.
Figure 6:
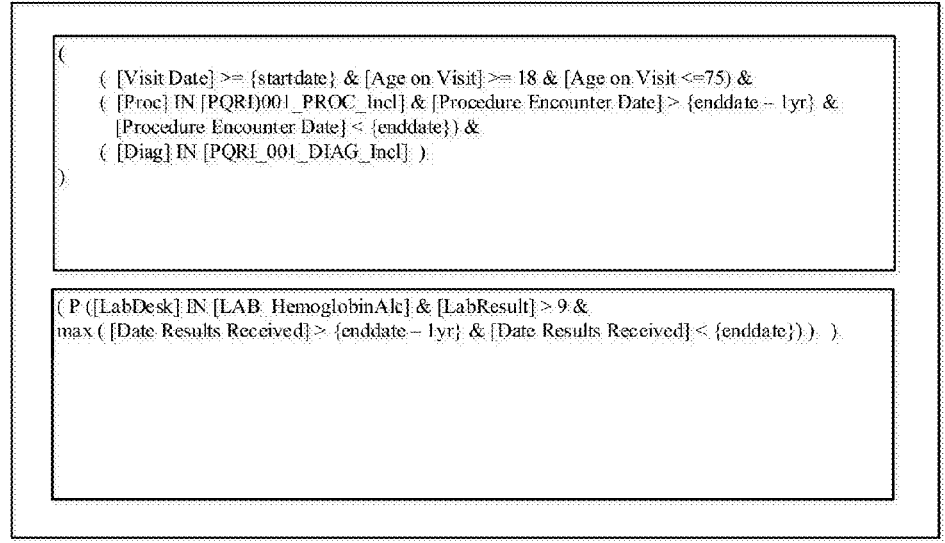
FIG. 6 is an interface for building a measure.

FIG. 5 is a schematic of a method 500 for using the HQM client 290 and HQM Service 250 (see FIG. 2). First, a provider builds a measure using measure builder 264. FIG. 6 shows an interface 600 for displaying a measure expression. Interface 600 allows the health care provider to build and view a measure expression without the need for SQL queries (i.e., the expression does not need to be an SQL query or equivalent format), thus obviating the need to learn a complex program language. Interface 600 includes drag-and-drop and point-and-click functionality. Second, the expression parts (see FIG. 6) are translated into SQL queries and list are generated for each measure using HQM client 290. FIG. 7 shows an interface 700 for displaying the conversion of the measure expressions into SQL queries. Third, the generated lists are converted from infix notation into postfix notation (reverse polish notation) and the lists are merged. FIG. 8 shows an interface 800 for converting and displaying a measure expression as a postfix notation reverse polish algorithm. Finally, the merged lists are displayed in numerator and denominator counts and lists. FIG. 9 shows an interface 900 for displaying patient counts and lists.

Method 500 allows providers to build measures and report measures to many different health organizations, each using their own proprietary format, all without the need to know SQL programming. Method 500 also allows HQM client 290 and HWM service 250 to record mappings between different formats of provider-defined measures.

One should appreciate that the various elements or functionality of the disclosed system can be moved from one location (e.g., provider, HQM engine, organization, etc.) to another without departing from the main concepts of the inventive subject matter. All arrangements of functionality are contemplated. Furthermore, one should also appreciate that the disclosed elements can be embodied by hardware or software installable at the various sites (e.g., the provider site, HQM service site, organization site, etc.)

Thus, specific compositions and methods of the inventive subject matter have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A method of reporting health quality measures (HQMs) to a funding organization, the method comprising:
   providing access to an HQM client capable of converting patient data stored on a healthcare provider's patient database from a proprietary format to a common HQM data format;
   providing a healthcare organization interface coupled to the HQM client;
   receiving, by the HQM client, first patient data in a first proprietary format from a first provider and second patient data in a second proprietary format from a second provider;
   generating, by the HQM client, first normalized patient data and second normalized patient data by normalizing the first and second patient data from their respective first and second proprietary formats to the common HQM data format;
   defining an HQM expression for generating HQMs based on different patient data types according to requirements set forth by the funding organization;
   deriving, by the HQM client, a plurality of first HQMs for the first provider and a plurality of second HQMs for the second provider according to the HQM expression and based on the different patient data types, wherein the plurality of first HQMs are derived from the first normalized patient data and the plurality of second HQMs are derived from the second normalized patient data;
   generating, by the HQM client, a presentation package comprising the plurality of first and second HQMs and the normalized first and second patient data; and
   presenting the package to the funding organization.

2. The method of claim 1, further comprising authenticating the funding organization with respect to the HQM client.

3. The method of claim 1, wherein the HQM expression is defined by the first and second providers.

4. The method of claim 3, wherein the step of defining the HQM expression comprises allowing the first provider to drag and drop elements of selection criteria to form the HQM expression.

5. The method of claim 1, wherein the HQM expression is defined by the funding organization.

6. The method of claim 1, wherein the step of deriving the plurality of first HQMs comprises calculating a numerator representing a number of encounters in the first normalized patient data that satisfy selection criteria of a numerator portion of each of the first HQMs, and calculating a denominator representing a number of encounters in the first normalized patient data that satisfy selection criteria of a denominator portion of the first HQMs.

7. The method of claim 6, further comprising calculating each of the first HQMs as a ratio of the numerator to the denominator.

8. The method of claim 6, the step of deriving the plurality of first HQMs further comprises generating a plurality of lists containing encounter data entries obtained from the first normalized patient data where each of the entries represents an encounter that satisfies individual selection criterion of the selection criteria from at least one of the numerator portion and the denominator portion.

9. The method of claim 8, wherein the plurality of first HQMs is derived based on at least some of the plurality of lists.

10. The method of claim 6, wherein the denominator portion and the numerator portion are expressed as a non-SQL query.

11. The method of claim 6, further comprising the step of converting the denominator portion and the numerator portion into an SQL query.

12. The method of claim 6, further comprising the step of converting the denominator portion and the numerator portion into a postfix notation reverse polish algorithm.

13. The method of claim 1, wherein the step of defining the HQM expression includes providing a point and click elements of selection criteria within the organization interface to form the HQM expression.

14. The method of claim 1, wherein the step of generating the presentation package includes automatically formatting the first and second HQMs according to the organization's requirements.

* * * * *